(12) United States Patent
Haibach

(10) Patent No.: US 9,339,623 B2
(45) Date of Patent: May 17, 2016

(54) EXHAUST GAS ASSEMBLY FOR A PATIENT INTERFACE DEVICE

(75) Inventor: Richard Thomas Haibach, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 276 days.

(21) Appl. No.: 13/879,079

(22) PCT Filed: Oct. 17, 2011

(86) PCT No.: PCT/IB2011/054583
§ 371 (c)(1),
(2), (4) Date: Apr. 12, 2013

(87) PCT Pub. No.: WO2012/052902
PCT Pub. Date: Apr. 26, 2012

(65) Prior Publication Data
US 2013/0213401 A1  Aug. 22, 2013

Related U.S. Application Data

(60) Provisional application No. 61/405,799, filed on Oct. 22, 2010.

(51) Int. Cl.
*A61M 16/06* (2006.01)
*A61M 16/00* (2006.01)
*A61M 16/08* (2006.01)

(52) U.S. Cl.
CPC ....... *A61M 16/0683* (2013.01); *A61M 16/0057* (2013.01); *A61M 16/06* (2013.01);
(Continued)

(58) Field of Classification Search
CPC ............ A61M 16/00; A61M 16/0057; A61M 16/0066; A61M 16/0069; A61M 16/009; A61M 16/04; A61M 16/0488; A61M 16/0493; A61M 16/06; A61M 16/0605; A61M 16/0611; A61M 16/0616; A61M 16/0622; A61M 16/0633; A61M 16/0638; A61M 16/0666; A61M 16/0683; A61M 16/08; A61M 16/0816; A61M 16/0825; A61M 16/0841; A61M 16/085; A61M 16/0858; A61M 16/0875; A61M 16/1065; A61M 16/109; A61M 16/1095; A61M 16/20; A61M 16/208; A61M 35/00; A61M 39/10; A62B 18/00; A62B 18/02; A62B 18/08; A62B 18/10; A62B 7/00; A62B 9/02; A62B 9/04; F16K 27/00
USPC ............ 128/205.25, 206.21, 206.24, 206.26, 128/207.11, 207.12, 207.13
See application file for complete search history.

(56) References Cited

U.S. PATENT DOCUMENTS 7,546,837 B2 * 6/2009 Busch et al. ............. 128/206.24
2004/0112385 A1 * 6/2004 Drew et al. ............... 128/206.21
(Continued)

FOREIGN PATENT DOCUMENTS

CN          1784250 A    6/2006
EP          2027880 A1   2/2009
(Continued)

*Primary Examiner* — Annette Dixon
(74) *Attorney, Agent, or Firm* — Michael W. Haas

(57) ABSTRACT

A patient interface device (2, 60, 160, 204) includes a cushion (8, 66, 210), a frame (10, 68, 162, 206) having a faceplate portion. The cushion is coupled to the frame. The faceplate portion has a main orifice and holes adjacent the main orifice. The device further includes a coupling conduit (6, 64, 164, 212) having an inlet end, an outlet end coupled to the inlet end, and a hood member having openings provided on an outer periphery thereof. The inlet end is structured to receive a flow of breathing gas. The outlet end is coupled to the main orifice to deliver the flow of breathing gas to the main conduit. The hood member surrounds the outlet end and is disposed over the holes such that exhalation gasses will through the holes and be captured by the hood member and directed through the openings.

20 Claims, 12 Drawing Sheets

(52) U.S. Cl.
CPC ....... *A61M16/0633* (2014.02); *A61M 16/0816* (2013.01); *A61M 16/0875* (2013.01); *A61M 2205/42* (2013.01)

(56) References Cited

U.S. PATENT DOCUMENTS

| | | |
|---|---|---|
| 2007/0062536 A1 | 3/2007 | McAuley |
| 2008/0066745 A1 | 3/2008 | Janbackhsh |
| 2008/0072910 A1 | 3/2008 | Janbakhsh |
| 2008/0210241 A1 | 9/2008 | Schulz |
| 2009/0272380 A1 | 11/2009 | Jaffre |
| 2010/0043796 A1 | 2/2010 | Meynink |
| 2010/0163049 A1 | 7/2010 | Osier |

FOREIGN PATENT DOCUMENTS

| | | |
|---|---|---|
| WO | WO2004096332 A1 | 11/2004 |
| WO | WO2007012140 A1 | 2/2007 |
| WO | WO2008058330 A1 | 5/2008 |
| WO | WO2011003130 A1 | 1/2011 |

* cited by examiner

EXHAUST GAS ASSEMBLY FOR A PATIENT INTERFACE DEVICE

CROSS-REFERENCE TO RELATED APPLICATIONS

This patent application claims the priority benefit under 35 U.S.C. §371 of international patent application no. PCT/IB2011/054583, filed Oct. 17, 2011, which claims the priority benefit under 35 U.S.C. §119(e) of U.S. Provisional Application No. 61/405,799 filed on October 22, 2010, the contents of which are herein incorporated by reference.

BACKGROUND OF THE INVENTION

1. Field of the Invention

The present invention relates to non-invasive ventilation and pressure support systems, and, in particular, to a patient interface device that may be used with such system to deliver gas to a patient that includes an exhaust gas assembly for reducing noise caused by patient exhalation and/or diffusing the patient exhalation flow.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component typically having a soft, flexible cushion on the face of a patient. The mask component may be, without limitation, a nasal mask that seals around the patient's nose, a nasal cushion having nasal prongs that are received within the patient's nares, a nasal/oral mask that seals over the nose and mouth, or a total face mask that seals around the patient's face. Such patient interface devices may also employ other patient contacting components, such as forehead supports, cheek pads and chin pads.

The patient interface device is connected to a gas delivery hose and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Such patient interface devices also include an exhaust gas assembly for exhausting a flow of gas from the patient interface device and/or gas delivery hose to the ambient atmosphere. This is necessary to flush the patient's exhaled $CO_2$ from the mask and/or gas delivery hose. While numerous different configurations for such exhaust gas assemblies are known, conventional exhaust gas assemblies can suffer excessive noise as the flow of exhaust gas passes through the exhaust gas assembly. This noise is undesirable in that it may disturb the sleep of the patient or the patient's bed partner.

Another problem associated with conventional exhaust gas assemblies is that stream of gas exiting the exhaust gas assembly can disturb the patient or the patient's bed partner. For example, the stream of gas, if directed into the eyes, or other sensitive part of the patient or the patient's bed partner can be annoying and/or uncomfortable.

SUMMARY OF THE INVENTION

Accordingly, it is an object of the present invention to provide a patient interface device with an exhaust gas assembly that overcomes the shortcomings of conventional patient interface devices. This object is achieved according to one embodiment of the present invention by providing a patient interface device that includes a cushion and a frame having a faceplate portion in which the cushion is coupled to the frame. The faceplate portion has a main orifice and one or more holes adjacent the main orifice. The main orifice and the one or more holes extend through the frame. The patient interface device further includes a fluid coupling conduit having an inlet end, an outlet end fluidly coupled to the inlet end, and a hood member having one or more openings provided on an outer periphery thereof. The inlet end is structured to receive a flow of breathing gas, and the outlet end is fluidly coupled to the main orifice to deliver the flow of breathing gas to the main orifice. The hood member surrounds the outlet end, is disposed over the one or more holes, and engages the faceplate portion in a manner wherein exhalation gasses will flow through the one or more holes and be captured by the hood member and directed through the one or more openings.

In another embodiment, a method of controlling gas flow through a patient interface device is provided that includes delivering a positive pressure flow of breathing gas to a patient through a coupling conduit fluidly coupled to a main orifice provided in a faceplate portion of the patient interface device, directing exhaled gasses exhaled by the patient to pass through one or more holes provided in the faceplate portion adjacent the main orifice, capturing the exhaled gasses in a chamber formed over the one or more holes and the main orifice, and directing the exhaled gasses through one or more openings provided in the chamber to atmosphere.

In yet another embodiment, a patient interface device is provided that includes a cushion and a frame having a faceplate portion, wherein the cushion is coupled to the frame. The faceplate portion has a main orifice and one or more holes adjacent the main orifice, the main orifice and the one or more holes extending through the frame. The patient interface device in this embodiment also includes a fluid coupling conduit having an inlet end, an outlet end terminating in an outlet opening, the outlet end being fluidly coupled to the inlet end, and a deflector member provided around an at least a portion of an outer periphery of the outlet end at a location spaced from the outlet opening. The inlet end is structured to receive a flow of breathing gas, and the outlet end is fluidly coupled to the main orifice to deliver the flow of breathing gas to the main orifice through the outlet opening. The deflector member is positioned over the one or more holes in a manner wherein exhalation gasses will flow through the one or more holes, and will be redirected and diffused by the deflector member and be caused to flow around the outlet end to atmosphere.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
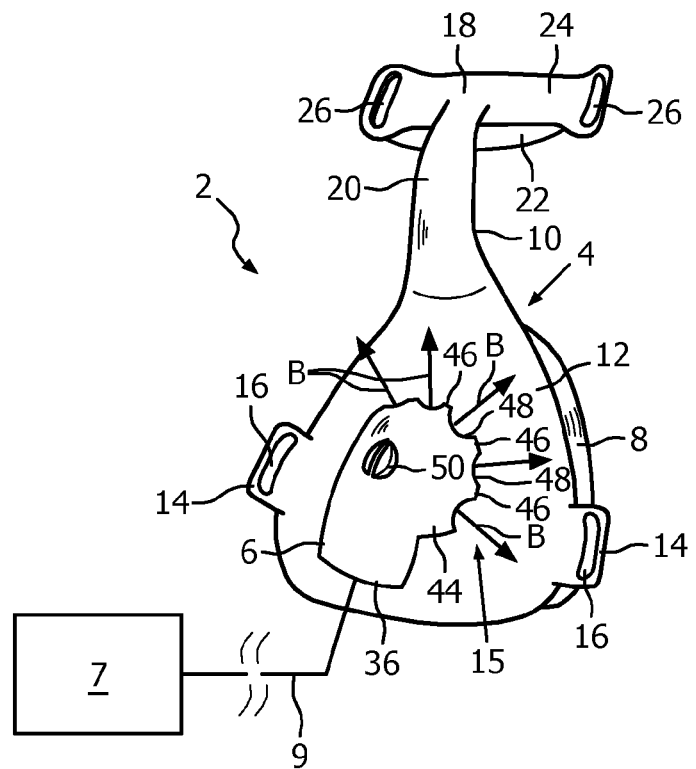
FIG. 1 is a front isometric view of a patient interface device according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a front isometric view of a patient interface device 2 according to one exemplary embodiment of the present invention. Patient interface device 2 includes a mask 4 that is fluidly coupled to an elbow conduit 6 in the manner described in greater detail elsewhere herein. Elbow conduit 6 is structured to be coupled to a suitable hose (also referred to as a patient circuit), which, in turn, is coupled to a suitable pressure generating device 7, which may include, without limitation, a constant pressure support device (such as a continuous positive airway pressure device, or CPAP device), a variable pressure device (e.g., BiPAP®, Bi-Flex®, or C-Flex™ devices manufactured and distributed by Philips Respironics of Murrysville, Pa.), an auto-titration pressure support device, a ventilator, or any other device that generates a flow of gas for delivery to an airway of a user.

Figure 2:
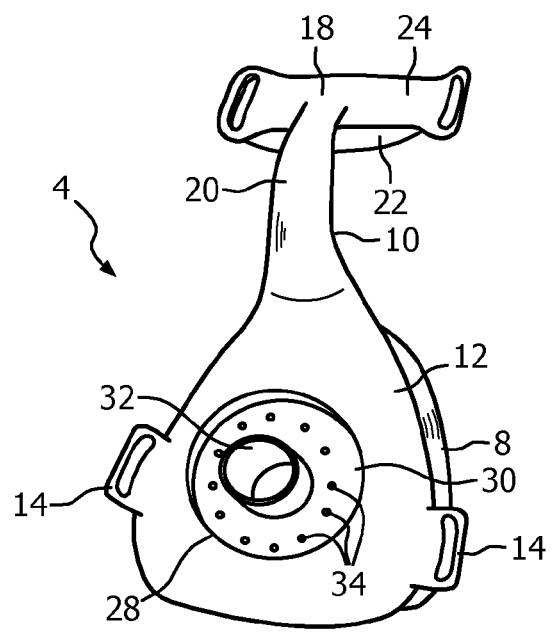
FIG. 2 is a front isometric view of a mask forming part of the patient interface device of FIG. 1.
Figure 3:
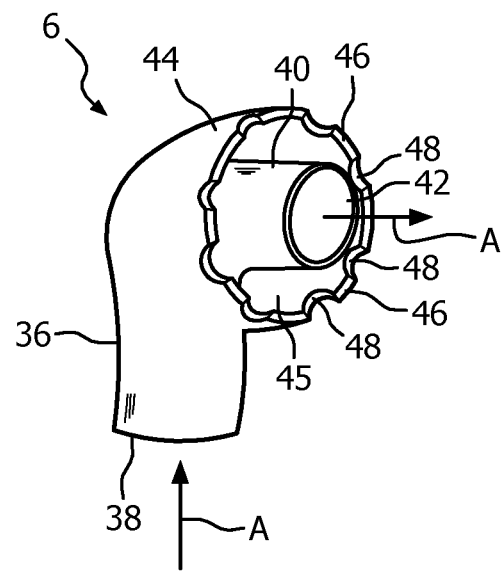
FIGS. 3 and 4 are rear and front isometric views, respectively, of an elbow conduit forming a part of the patient interface device of FIG. 1.
Figure 4:
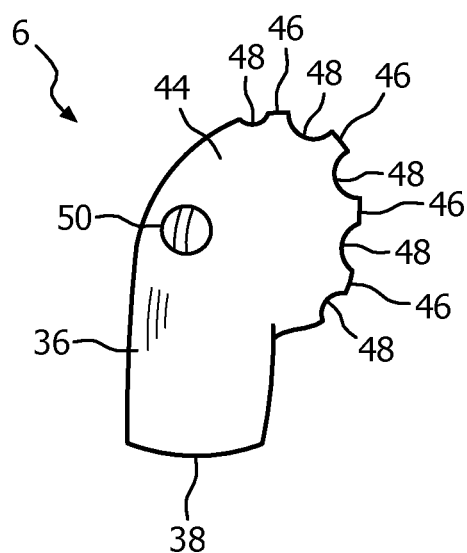

A hose or flexible conduit, also referred to as a patient circuit 9 (shown schematically in FIG. 1) couples the outlet of pressure generating device 7 to patient interface device 2. FIG. 2 is a front isometric view of mask 4 of patient interface device 2, and FIGS. 3 and 4 are rear and front isometric views, respectively, of elbow conduit 6 of patient interface device 2.

In the illustrated embodiment, mask 4 is a nasal/oral (full face) mask; meaning that, in use, it seals over both the nares and the mouth of the user. However, other types of masks, such as a nasal mask or a total face mask that seals around the entire face, or any other mask or patient interface device that facilitates the delivery of a flow of breathing gas to the airway of a patient may be used as mask 4 while remaining within the scope of the present invention.

Mask 4 includes a sealing cushion 8 that is operatively coupled to a frame 10. In the illustrated embodiment, sealing cushion 8 is defined from a unitary piece of soft, flexible, cushiony, elastomeric material, such as, without limitation, silicone, an appropriately soft thermoplastic elastomer, gel, a closed cell foam, or any combination of such materials. Frame 10 is made of a rigid or semi-rigid material, such as, without limitation, an injection molded thermoplastic or silicone, and includes a faceplate portion 12 to which elbow conduit 6 is attached. Faceplate portion 12 is described in greater detail below.

Frame 10 includes a pair of headgear connecting members 14 located on opposite sides of faceplate portion 12. Headgear connecting member are used to couple a headgear strap (not shown) to the mask. In the illustrated exemplary embodiment, each headgear connecting member 14 includes a loop 16 that is structured to receive a respective lower headgear strap of a headgear assembly (not shown) for securing patient interface device 2 to the head of the patient. It is to be understood that the present invention contemplates using any technique to attach a headgear to the frame, such as snaps, hooks, and ball-and-socket connectors, and is not to be limited to that shown.

Frame 10 further includes a forehead support 18 attached to extension member 20 extending from faceplate portion 12. Forehead support 18 includes a forehead cushion 22 that is coupled to a support frame 24. In an exemplary embodiment, forehead cushion 22 is made of a soft, flexible, elastomeric material, such as, without limitation, silicone rubber, an appropriately soft thermoplastic elastomer, or any combination of such materials, and, in the exemplary embodiment, is over-molded onto support frame 24.

Forehead support 18 is structured to provide additional support for patient interface device 2 by engaging the forehead of the patient. Support frame 24 includes headgear connecting members 26 provided at opposite ends thereof. In the illustrated embodiment, headgear connecting members 26 are configured as a loop that is structured to receive a respective upper headgear strap of a headgear assembly (not shown) for securing patient interface device 2 to the head of the patient. It is to be understood that the present invention contemplates other configurations for forehead support 18, support frame 24, and headgear connecting members 26. In the illustrated embodiment, forehead support 18 is shown as a unitary member with frame 10. The present invention contemplates, however, that the forehead support can be adjustable relative to the frame as is known in the art. In addition, the present invention contemplates omitting the forehead support structure entirely.

Referring to FIG. 2, faceplate portion 12 includes a gas flow region 28 through which both breathing gas for the patient supplied by the pressure generating device and exhalation gasses exhaled by the patient may flow. In the exemplary embodiment, gas flow region 28 includes a recessed portion 30 that surrounds a main conduit 32. The present invention contemplates that faceplate portion 12, including gas flow region 28 and recessed portion 30 are formed as a unitary component. It to be understood that the various components of the faceplate can be formed as separate components and assembled together to define the entire faceplate portion. For example, gas flow region including recessed portion 30 and main conduit 32 can be formed from a separate component that is assembled with the rest of the faceplate. The advantage of using separate components is that the various component can be readily altered or replaced without having to replace the entire faceplate portion.

Main conduit 32 extends through faceplate portion 12 to communicate a flow of gas from hose 9 to the interior of mask 4. As described in greater detail below, main conduit 32 is structured to be coupled to elbow conduit 6 for receiving the flow of breathing gas therefrom. In addition, recessed portion 30 includes one or more holes 34 that extend through faceplate portion 12. Holes 34 define a portion of the exhaust gas assembly. In the exemplary embodiment, recessed portion 30 includes a plurality of holes 34 that are positioned close to and surround main conduit 32. The present invention contemplates other configurations for the location of the holes within gas flow region 28. Also in the exemplary embodiment, holes 34 are circular in shape, but other shapes are possible. As can be appreciated, recessed portion 30 is optional so long as gas can flow from the cavity defined by faceplate portion 12 and into the area formed between the faceplate portion 12 and elbow conduit 6 for exhausting to the ambient atmosphere. See, e.g., FIG. 14, which omits any such recessed portion.

Figure 16:
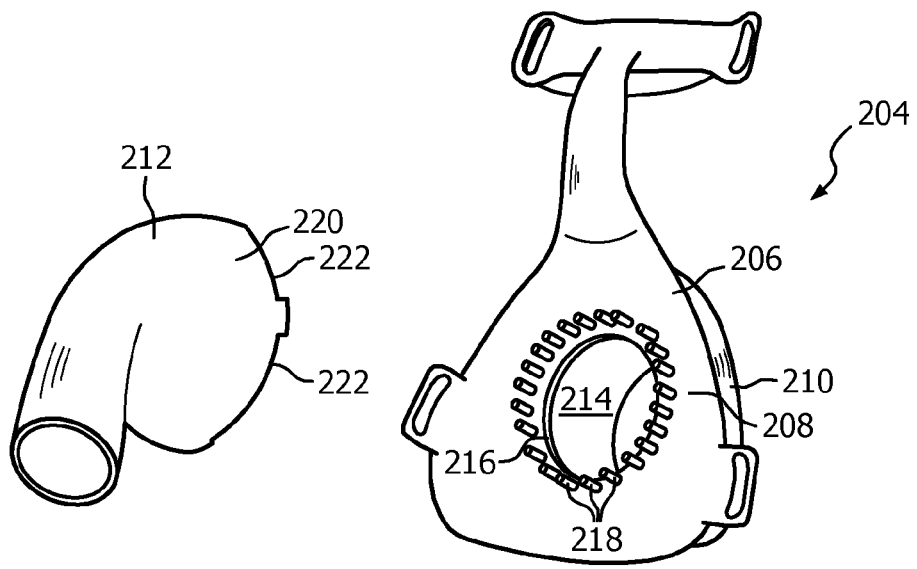
FIG. 16 is a front isometric view of a patient interface device according to a further alternative embodiment of the present invention.
Figure 17:
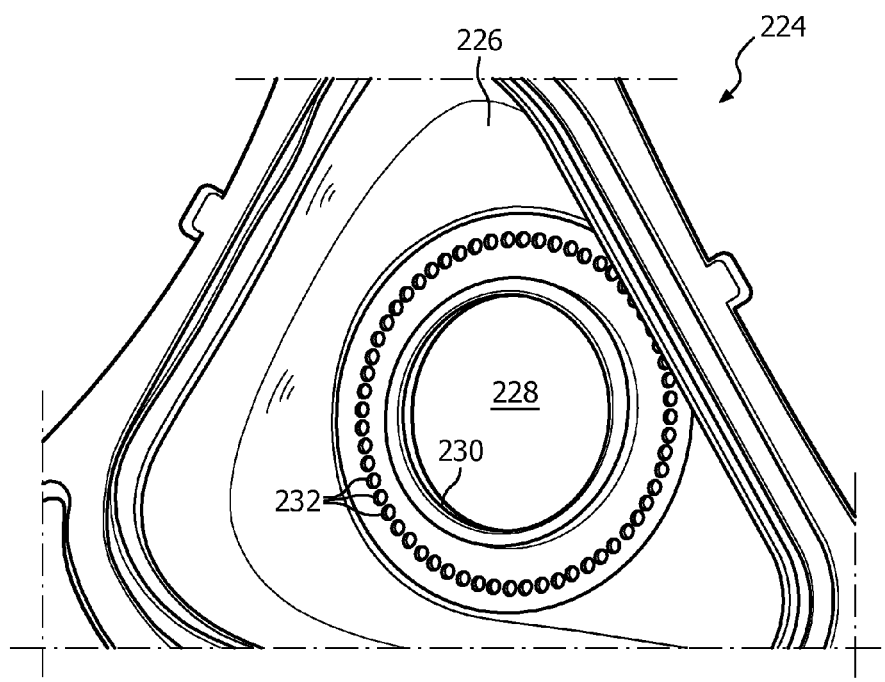
FIG. 17 is a rear isometric view of a portion of a frame according to another alternative embodiment that may be employed in the present invention.

The depth of holes 34 may be equal to the thickness of faceplate portion 12, or, alternatively, holes 34 could be formed into tube-like passageways or chamfered openings that extend longer than the thickness of faceplate portion 12 and, thus, outwardly from faceplate portion 12 or into the space created by the interior of cushion 8 (see, for example, FIGS. 16 and 17 described elsewhere herein). In the exemplary embodiment, the diameter of holes 34 is such that they restrict or control the flow of exhalation gasses as they exit cushion 8. For example, the diameter of holes 34 may be from 0.5 mm to 2.5 mm. In one exemplary embodiment, sixty holes 34 are provided, wherein each hole has a diameter of 0.6 mm. In another exemplary embodiment, four holes 34 are provided, wherein each hole has a diameter of 2.0 mm.

Referring to FIGS. 3 and 4, elbow conduit 6 includes an inlet end 36 having an inlet opening 38 structured to be connected to the hose connected to the pressure generating device. Elbow conduit 6 also includes an outlet end 40 having an outlet opening 42 that is in fluid communication with inlet end 36 and inlet opening 38. Outlet end 40 is structured to be removeably and sealingly coupled to main conduit 32. In the example embodiment, outlet end 40 may be provided with an o-ring for providing an airtight seal.

In addition, elbow conduit 6 includes a hood member 44 that surrounds outlet end 40. Hood member 44 is not in fluid communication with inlet opening 38, but rather engages the inner portion of outlet end 40 such that it defines an interior space 45 around outlet end 40 that is not in fluid communication with inlet opening 38. Hood member 44 includes a plurality of contacting edges 46 that define between them a plurality of hemispherical openings 48, the purpose of which is described below. In the illustrated embodiment, elbow conduit 6 includes optional entrainment valve 50.

Referring again to FIG. 1, elbow conduit 6 may be attached to mask 4 by inserting outlet end 40 into main conduit 32. When this is done, contacting edges 46 will contact the outer surface of faceplate portion 12, and in the exemplary embodiment will create a seal against that surface. In addition, as seen in FIG. 1, hood member 44 is disposed over holes 34 and main conduit 32.

In operation, a flow of gas provided by the pressure generating device is delivered to mask 4 through elbow conduit 4, and, in particular, inlet end 36 and outlet end 40 through main conduit 32 as indicated by arrows A. When the patient exhales, the flow of exhalation gas pass through holes 34 and are captured and redirected by hood member 44 (which creates a chamber) and will be caused to pass to the ambient atmosphere through hemispherical openings 48 as indicated by arrow B in FIG. 1. This configuration of components for the mask diffuses the exhalation flow to avoid the creation of a stream of gas that can be annoying if directed onto the skin of the user or the user's bed partner. In short, the passage of gas through holes 34 into a buffering chamber defined by space 45 between hood 44 and faceplate 10 and the subsequent passage of the gas through holes/spaces/openings 48 creates a plume of exhaust gas at or around the elbow conduit. The large size of this plume maximizes the dispersion of the exhaust gas flow to the ambient atmosphere thereby avoiding the creation of potentially annoying streams of exhaust gas.

Noise is created as the exhalation gasses pass through holes 34. However, hood member 44 creates an insulating wall between the sound generated as gas passes through holes 34 and the atmosphere. This noise attenuation barrier effectively reduces the noise perceived by the user and/or bed partner and changes the tone of the noise to a tone that is better tolerated by individuals located nearby. Also, hood member 44 causes the sound waves associated with the exhalation flow to be reflected within the patient interface device, which results in a further degree of noise cancellation.

Figure 5:
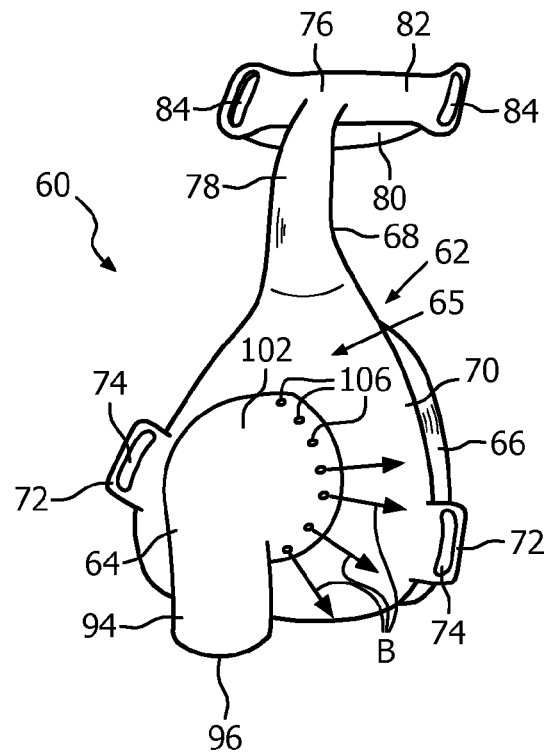
FIG. 5 is a front isometric view of a patient interface device according to another exemplary embodiment of the present invention.
Figure 6:
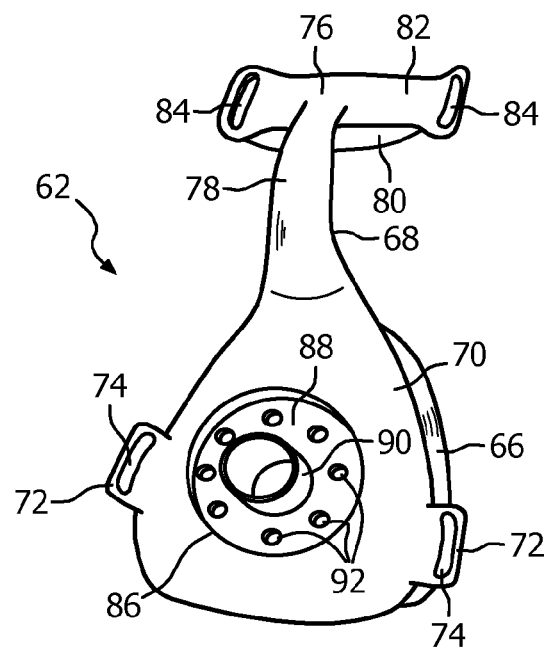
FIG. 6 is a front isometric view of a mask forming part of the patient interface device of FIG. 5.
Figure 7:
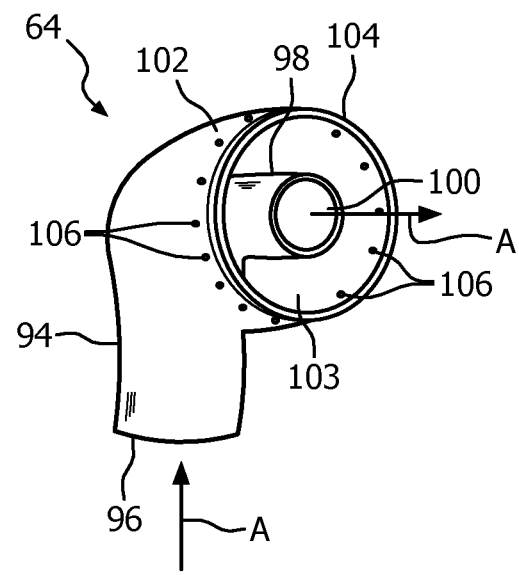
FIGS. 7 and 8 are rear and front isometric views, respectively, of an elbow conduit forming a part of the patient interface device of FIG. 5.
Figure 8:
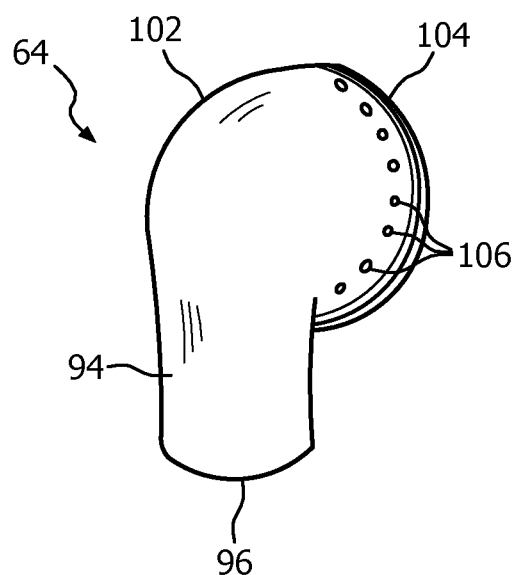

FIG. 5 is a front isometric view of a patient interface device 60 according to another exemplary embodiment of the present invention. Patient interface device 60 includes a mask 62 that is fluidly coupled to an elbow conduit 64 in the manner described in greater detail elsewhere herein. Elbow conduit 64 is structured to be coupled to a suitable hose, which in turn is coupled to a suitable pressure generating device as described elsewhere herein. FIG. 6 is a front isometric view of mask 62 of patient interface device 60, and FIGS. 7 and 8 are rear and front isometric views, respectively, of elbow conduit 64 of patient interface device 60.

In the illustrated embodiment, mask 62 is a nasal/oral mask. However, other types of masks, such as a nasal mask or a full face mask, which facilitate the delivery of a flow of breathing gas to the airway of a patient, may be used as mask 62 while remaining within the scope of the present invention. Mask 62 includes a sealing cushion 66 coupled to a frame 68. In the illustrated embodiment, sealing cushion 66 is defined from a unitary piece of soft, flexible, cushiony, elastomeric material, such as, without limitation, silicone, an appropriately soft thermoplastic elastomer, a closed cell foam, or any combination of such materials. Frame 68 is made of a rigid or semi-rigid material, such as, without limitation, an injection molded thermoplastic or silicone, and includes faceplate portion 70 to which elbow conduit 64 is attached. Faceplate portion 70 is described in greater detail below.

Frame 68 includes a pair of connecting members 72 extending from opposites side of faceplate portion 70, wherein each connecting member 72 includes a loop 74 which is structured to receive a respective lower headgear strap of a headgear assembly (not shown) for securing patient interface device 60 to the head of the patient. Alternatively, rather than connecting members 72, frame 68 may be provided with quick release clips for attaching to headgear straps. Frame 68 further includes forehead support 76 attached to extension member 78 extending from faceplate portion 70. Forehead support 76 includes forehead cushion 80 that is coupled to support frame 82. Forehead cushion 80 is made of a soft, flexible, elastomeric material, such as, without limitation, silicone rubber, an appropriately soft thermoplastic elastomer, or any combination of such materials, and, in the exemplary embodiment, is over-molded onto support frame 82. Forehead support 76 is structured to provide additional support for patient interface device 60 by engaging the forehead of the patient. Support frame 82 includes loops 84 provided at opposite ends thereof. Each loop 84 is structured to receive a respective upper headgear strap of a headgear assembly (not shown) for securing patient interface device 60 to the head of the patient. It should be noted that the numerous variations for the components of the mask discussed above with respect to FIGS. 1-4 are equally applicable to the mask shown in FIGS. 5-7.

Referring now to FIG. 6, faceplate portion 70 includes a gas flow region 86 through which both breathing gas for the patient supplied by the pressure generating device and exhalation gasses exhaled by the patient may flow. Gas flow region 86 includes an optional recessed portion 88 that surrounds main conduit 90. Main conduit 90 extends through faceplate portion 70.

As described in greater detail below, main conduit 90 is structured to be coupled to elbow conduit 64 for receiving the flow of breathing gas therefrom. In addition, recessed portion 88 includes one or more holes 92 that extend through faceplate portion 70. In th exemplary embodiment, recessed portion 88 includes a plurality of holes 92 that are positioned close to and surround main conduit 90. Also in the exemplary embodiment, holes 92 are circular in shape, but other shapes are possible. The depth of holes 92 may be equal to the thickness of faceplate portion 70, or, alternatively, holes 92 could be formed into tube-like passageways or chamfered openings that extend longer than the thickness of faceplate portion 70 and thus into the space created by the interior of sealing cushion 66 as described elsewhere herein. In the exemplary, non-limiting embodiment, holes 92 are less restrictive than holes 34 of patient interface device 2.

Referring to FIGS. 7 and 8, elbow conduit 64 includes inlet end 94 having inlet opening 96 structured to be connected to the hose connected to the pressure generating device. Elbow conduit 64 also includes an outlet end 98 having an outlet opening 100 that is in fluid communication with an inlet end 94 and an inlet opening 96. Outlet end 98 is structured to be removeably and sealingly coupled to main conduit 90. In the example embodiment, outlet end 98 may be provided with an o-ring for providing an airtight seal. In addition, elbow conduit 64 includes a hood member 102 that surrounds outlet end 98.

Hood member 102 is not in fluid communication with inlet opening 96, but rather engages the inner portion of outlet end 98 such that it defines an interior space 103 around outlet end 40 that is not in fluid communication with inlet opening 38. Hood member an 102 includes outer edge 104 that is structured to sealingly engage the edge of recessed portion 88, and may include an o-ring for providing an airtight seal. Hood member 102 also includes one or more holes 106 that extend through hood member 102. In the exemplary embodiment, hood member 102 includes a plurality of holes 106 that are spaced around the perimeter of hood member 102.

Also in the exemplary embodiment, holes 106 are circular in shape, but other shapes are possible. In the exemplary embodiment, the diameter of holes 106 is such that they restrict or control the flow of exhalation gasses as they hood member 102. For example, the diameter of holes 106 may be from 0.5 mm to 2.5 mm. In one exemplary embodiment, sixty holes 106 are provided, wherein each hole has a diameter of 0.6 mm. In another exemplary embodiment, four holes 106 are provided, wherein each hole has a diameter of 2 mm. Although not shown, elbow conduit 64 may include an optional entrainment valve.

Referring again to FIG. 5, elbow conduit 64 may be attached to mask 62 by inserting outlet end 98 into main conduit 90. When this is done, outer edge 104 will sealingly engage the edge of recessed portion 88 of faceplate portion 70. In addition, as seen in FIG. 5, hood member 102 will is disposed over holes 92 and main conduit 90.

In operation, breathing gas generated by the pressure generating device will be delivered to mask 62 through elbow conduit 64, and in particular inlet end 94 and outlet end 98 through main conduit 90 as indicated by arrows A. When the patient exhales, exhalation gasses will pass through holes 92 and will be captured and redirected by hood member 102 (which creates a chamber) and will be caused to pass to the atmosphere through holes 106, which diffuse the exhalation flow as indicated by arrows B.

Noise is created as the exhalation gasses pass through holes 92, and hood member 102 creates an insulating wall between the sound and the atmosphere to reduce noise and change the tone of the noise to a tone that is better tolerated by individuals located nearby. Also, hood member 102 causes the sound waves associated with the exhalation flow to be reflected, which results in some degree of noise cancellation Furthermore, since holes 92 are, in the exemplary embodiment, spaced 360 degrees around main conduit 90, they cause the noise associated with the exhalation flow to be spread out and they provide for enhanced $CO_2$ flushing from mask 62. In other words, the path followed by the exhaust gas (path shown by arrows B) is separate and distinct from the path followed by the incoming gas (path shown by arrows A). As a result, the exhaust gas does not have to flow against the incoming gas flow. This results in $CO_2$ being readily flushed from mask.

In the embodiment shown in FIGS. 1-4, the size of holes 34 in the mask define the amount or resistance to flow for the exhaust gas assembly, which is generally indicated at 15 in FIG. 1. That is the size of holes 34, and not openings 48, determine the rate of flow of exhaust gas to ambient atmosphere for any given pressure. In the embodiment shown in FIGS. 5-7, the opposite is true. That is, the size of holes 106 in elbow conduit 5 define the amount or resistance to flow for the exhaust gas assembly, generally indicated at 65. That is, the size of holes 106, and not openings 92 defined in the faceplate, determine the rate of flow of exhaust gas to ambient atmosphere for any given pressure.

It should be noted that the a clearance between the mask shell and the edge of the hood can also define the amount or resistance to flow for the exhaust gas assembly. In other words, holes 106 in FIGS. 5-7 can be replaced with an opening and/or a clearance provided between hood member 102 and faceplate portion 70.

In one particular, non-limiting embodiment, elbow conduit 64 may include a series of baffles between hood member 102 and outlet end 98 to further quiet exhalation as described elsewhere herein.

Figure 9:
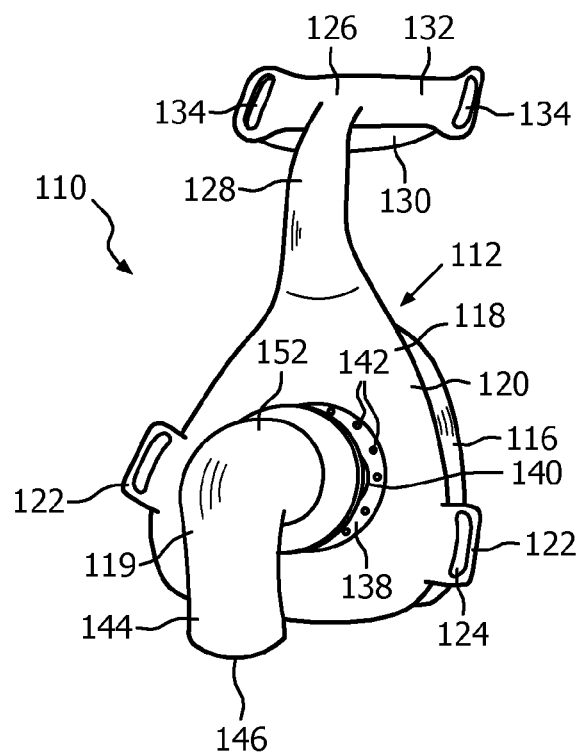
FIG. 9 is a front isometric view of a patient interface device according to an alternative exemplary embodiment of the present invention.
Figure 10:
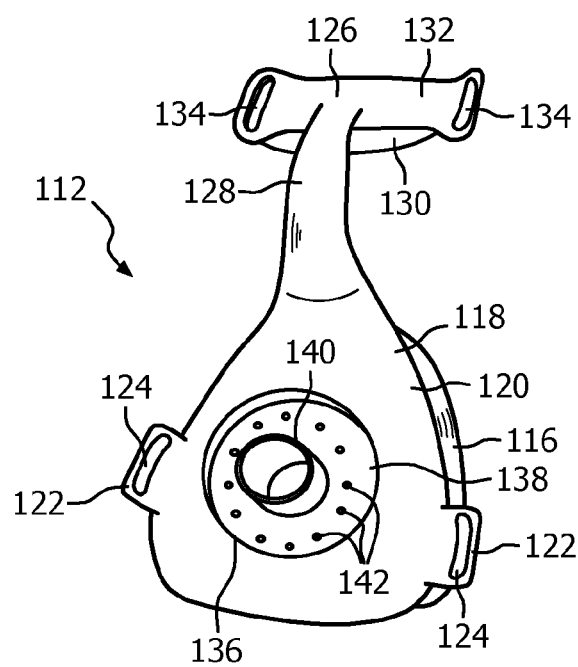
FIG. 10 is a front isometric view of a mask forming part of the patient interface device of FIG. 9.
Figure 11:
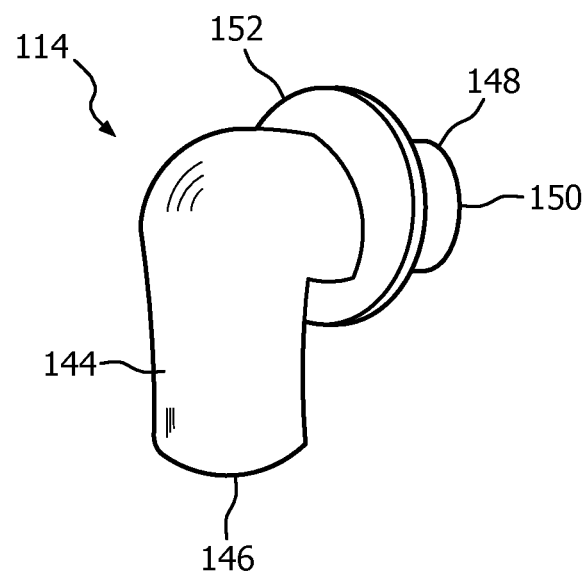
FIG. 11 is a rear isometric view of an elbow conduit forming a part of the patient interface device of FIG. 9.

FIG. 9 is a front isometric view of patient interface device 110 according to a further alternative exemplary embodiment of the present invention. Patient interface device 110 includes mask 112 that is fluidly coupled to elbow conduit 114 in the manner described in greater detail elsewhere herein. Elbow conduit 114 is structured to be coupled to a suitable hose, which in turn is coupled to a suitable pressure generating device as described elsewhere herein. FIG. 10 is a front isometric view of mask 112 of patient interface device 110, and FIG. 11 is a front isometric view of elbow conduit 114 of patient interface device 110.

In the illustrated embodiment, mask 112 is a nasal/oral mask. However, other types of masks, such as a nasal mask or a full face mask, which facilitate the delivery of a flow of breathing gas to the airway of a patient, may be used as mask 62 while remaining within the scope of the present invention. Mask 112 includes sealing cushion 116 which coupled to frame 118. In the illustrated embodiment, sealing cushion 116 is defined from a unitary piece of soft, flexible, cushiony, elastomeric material, such as, without limitation, silicone, an appropriately soft thermoplastic elastomer, a closed cell foam, or any combination of such materials. Frame 118 is made of a rigid or semi-rigid material, such as, without limitation, an injection molded thermoplastic or silicone, and includes faceplate portion 120 to which elbow conduit 114 is attached. Faceplate portion 120 is described in greater detail below.

Frame 118 includes a pair of connecting members 122 extending from opposites side of faceplate portion 120, wherein each connecting member 122 includes a loop 124 which is structured to receive a respective lower headgear strap of a headgear assembly (not shown) for securing patient interface device 110 to the head of the patient. Alternatively, rather than connecting members 122, frame 18 may be provided with quick release clips for attaching to headgear straps. Frame 118 further includes forehead support 126 attached to extension member 128 extending from faceplate portion 120. Forehead support 126 includes forehead cushion 130 that is coupled to support frame 132. Forehead cushion 130 is made of a soft, flexible, elastomeric material, such as, without limitation, silicone rubber, an appropriately soft thermoplastic elastomer, or any combination of such materials, and, in the exemplary embodiment, is over-molded onto support frame 132. Forehead support 126 is structured to provide additional support for patient interface device 110 by engaging the forehead of the patient. Support frame 132 includes loops 134 provided at opposite ends thereof. Each loop 134 is structured to receive a respective upper headgear strap of a headgear assembly (not shown) for securing patient interface device 110 to the head of the patient.

Referring to FIG. 10, faceplate portion 120 includes gas flow region 136 through which both breathing gas for the patient supplied by the pressure generating device and exhalation gasses exhaled by the patient may flow. Gas flow region 136 includes a recessed portion 138 that surrounds a main conduit 140. Main conduit 140 extends through faceplate portion 120.

As described in greater detail below, main conduit 140 is structured to be coupled to elbow conduit 114 for receiving the flow of breathing gas therefrom. In addition, recessed portion 138 includes one or more holes 142 that extend through faceplate portion 120. In the exemplary embodiment, recessed portion 120 includes a plurality of holes 142 that are positioned close to and surround main conduit 140. Also in the exemplary embodiment, holes 142 are circular in shape, but other shapes are possible. The depth of holes 142 may be equal to the thickness of faceplate portion 120, or, alternatively, holes 142 could be formed into tube-like passageways or chamfered openings that extend longer than the thickness of faceplate portion 120 as described elsewhere herein. In the exemplary embodiment, the diameter of holes 142 is such that they restrict or control the flow of exhalation gasses as they exit cushion 116. For example, the diameter of holes 142 may be from 0.5 mm to 2.5 mm. In one exemplary embodiment, sixty holes 142 are provided, wherein each hole has a diameter of 0.6 mm. In another exemplary embodiment, four holes 142 are provided, wherein each hole has a diameter of 2 mm.

Referring to FIG. 11, elbow conduit 114 includes an inlet end 144 having inlet opening 146 structured to be connected to the hose connected to the pressure generating device. Elbow conduit 14 also includes an outlet end 148 having an outlet opening 150 that is in fluid communication with inlet end 144 and inlet opening 150. Outlet end 148 is structured to be removeably and sealingly coupled to main conduit 140. In addition, elbow conduit 114 includes a deflector member 152 that is provided around the outer periphery of outlet end 148 a short distance (e.g., from 5 mm to 15 mm) away from outlet opening 150. In one embodiment, deflector member 152 is arced, and in another embodiment, deflector member 152 is flat.

Referring again to FIG. 9, elbow conduit 114 may be attached to mask 112 by inserting outlet end 148 into main conduit 142. When this is done, deflector member 152 will be positioned over holes 142 (in the exemplary embodiment, deflector member 152 will be positioned directly over holes 142 as shown in FIG. 9). A gap or chamber is defined between deflector member 152 and faceplate portion 120. In operation, breathing gas generated by the pressure generating device is delivered to mask 112 through elbow conduit 114, and in particular inlet end 146 and outlet end 148 through main conduit 140. When the patient exhales, exhalation gasses pass through holes 142 and into this gap. The gas is then redirected and diffused by deflector member 152 such that it flows around outlet end 148 of elbow conduit 114 as it is caused to pass to the atmosphere.

Figure 12:
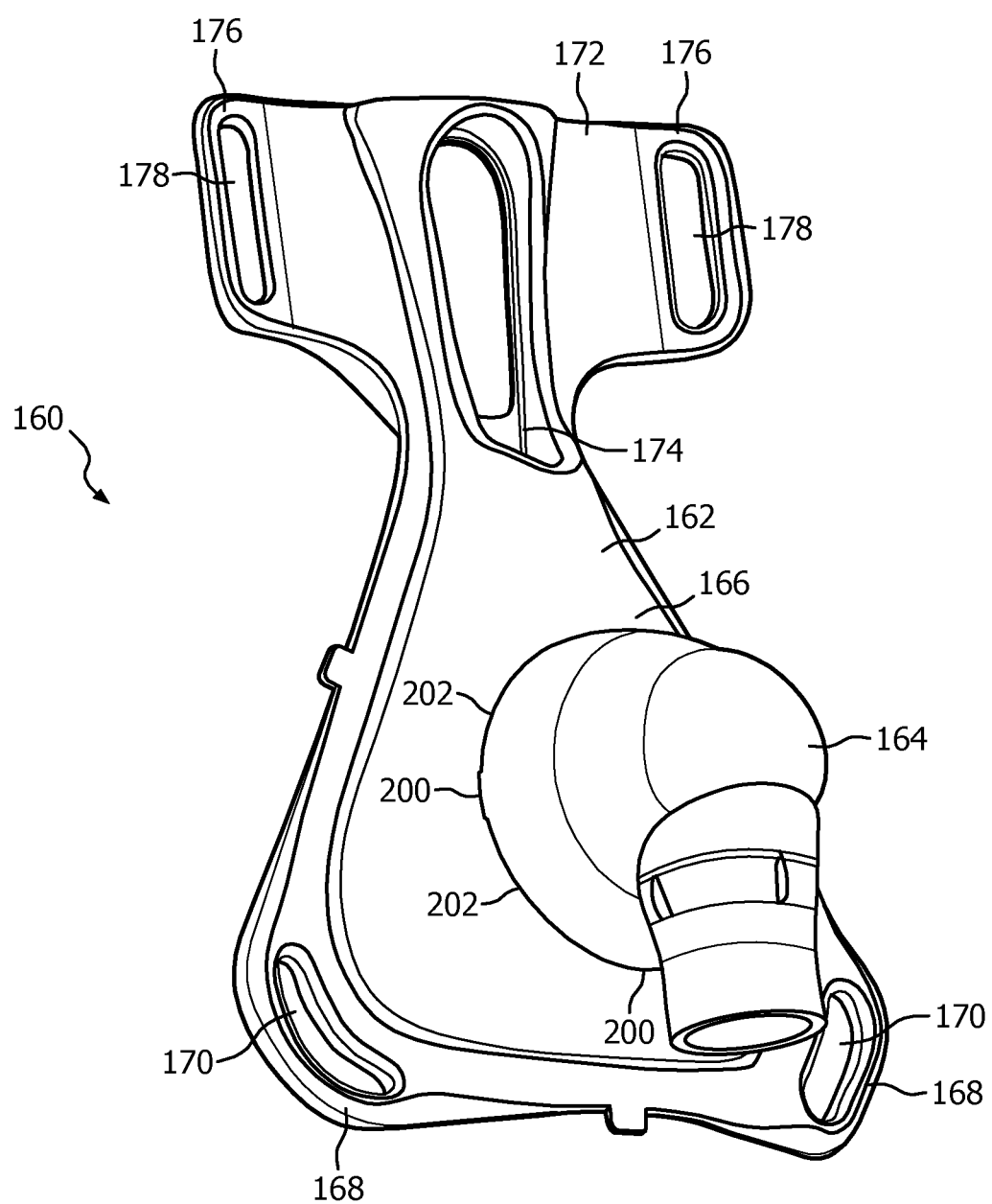
FIG. 12 is a front isometric view and FIG. 13 is a rear isometric view of a portion of a patient interface device according to another exemplary embodiment of the present invention.
Figure 13:
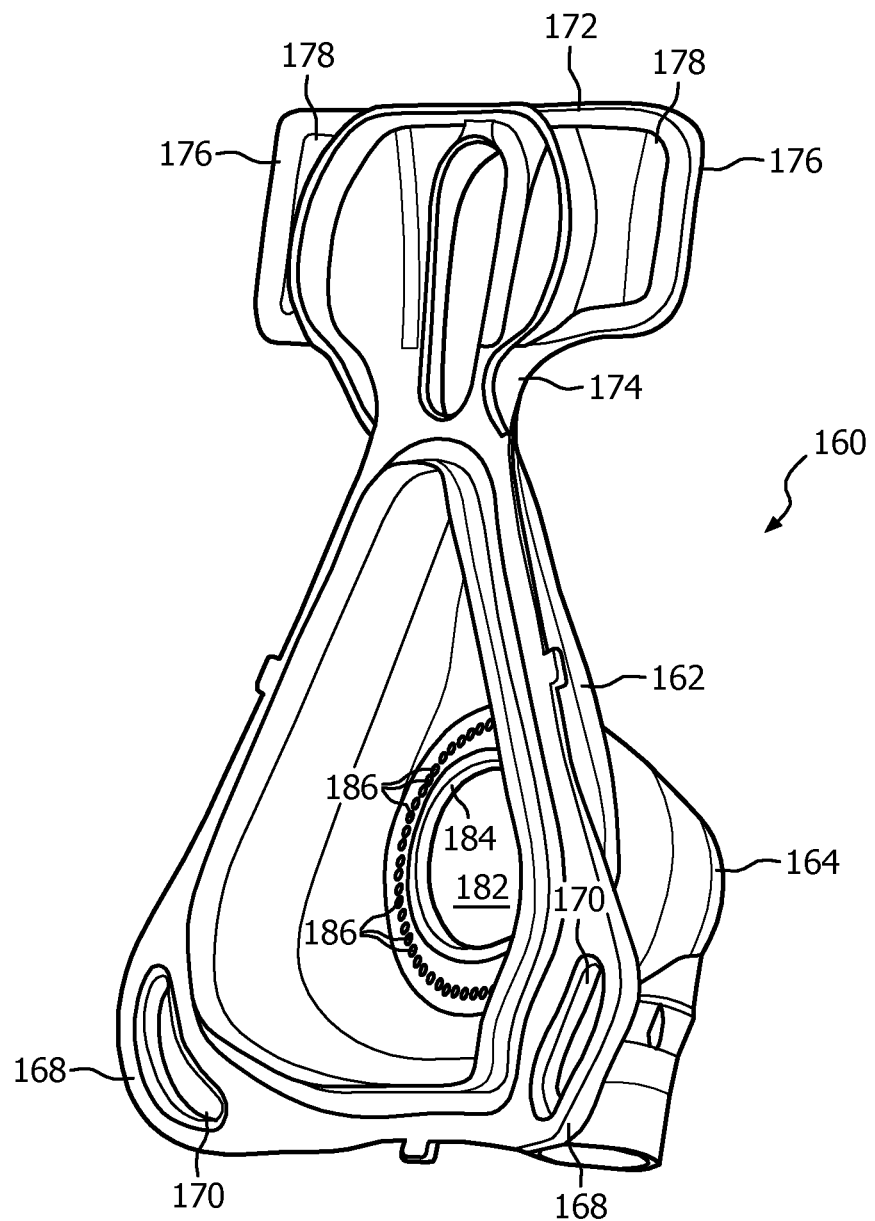

FIG. 12 is a front isometric view and FIG. 13 is a rear isometric view of a portion of a patient interface device 160 according to another exemplary embodiment of the present invention. As will be apparent from the following description, patient interface device 160 is similar to patient interface device 2 described elsewhere herein.

Figure 14:
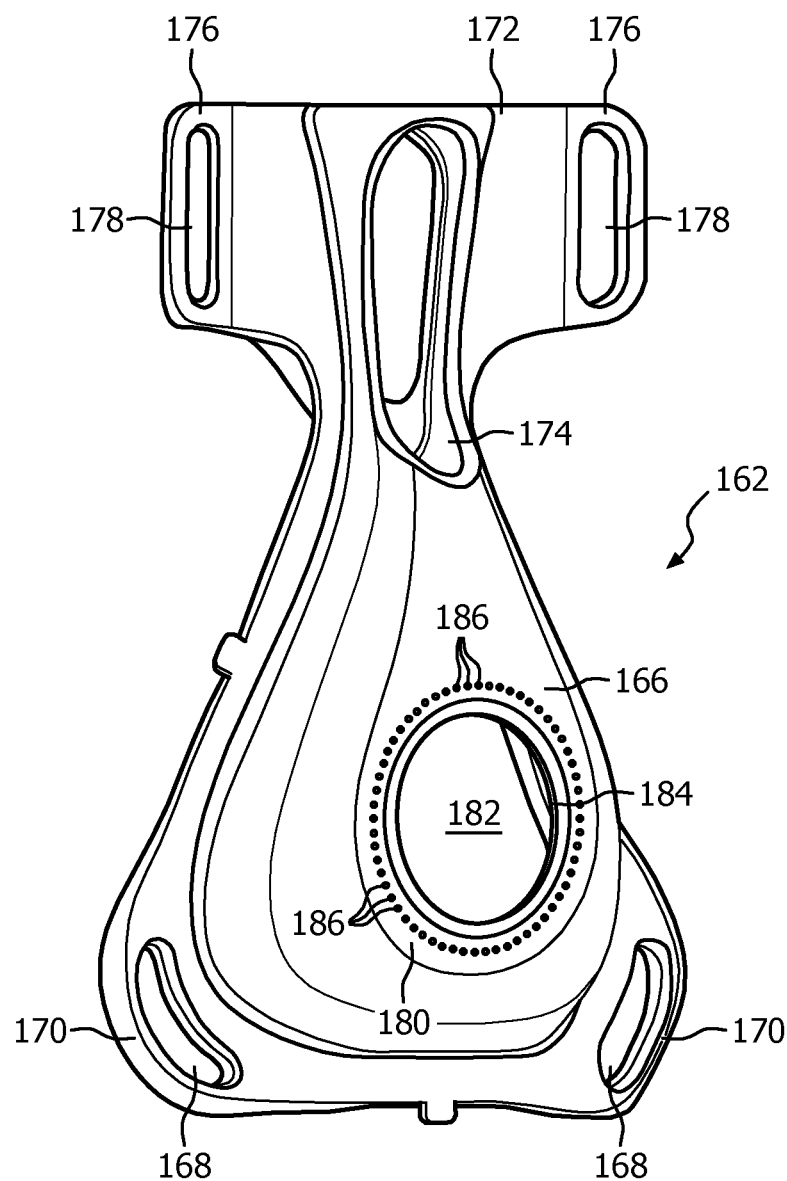
FIG. 14 is a front isometric view of a frame forming a part of the patient interface device of FIGS. 12 and 13.
Figure 15:
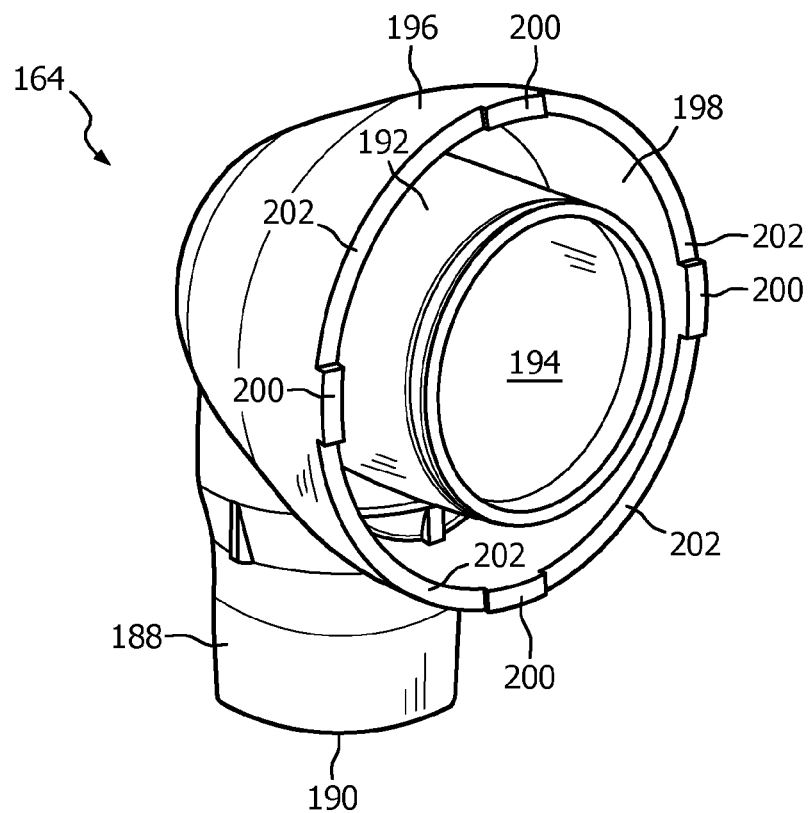
FIG. 15 is a rear isometric view of an elbow conduit forming a part of the patient interface device of FIGS. 12 and 13.

Patient interface device 160 includes a frame 162 to which a sealing cushion as described elsewhere herein (not shown) may be coupled. An elbow conduit 164 is coupled to frame 162 in the manner described in greater detail elsewhere herein. Elbow conduit 164 is structured to be coupled to a suitable hose, which in turn is coupled to a suitable pressure generating device. FIG. 14 is a front isometric view of frame 162, and FIG. 15 is a rear isometric view of elbow conduit 164.

Frame 162 is made of a rigid or semi-rigid material, such as, without limitation, an injection molded thermoplastic or silicone, and includes faceplate portion 166 to which elbow conduit 164 is attached. Faceplate portion 166 is described in greater detail below.

Frame 162 includes a pair of headgear connecting members 168 extending from opposites side of faceplate portion 166, wherein each headgear connecting member 168 includes a loop 170 which is structured to receive a respective lower headgear strap of a headgear assembly (not shown) for securing patient interface device 160 to the head of the patient. Frame 162 further includes a forehead support 172 attached to an extension member 174 extending from faceplate portion 166. Forehead support 172 includes a support frame 176 having headgear connecting members in the form of loops 178 provided at opposite ends thereof. Each loop 178 is structured to receive a respective upper headgear strap of a headgear assembly (not shown) for securing patient interface device 160 to the head of the patient.

Referring to FIG. 14, faceplate portion 166 includes a gas flow region 180 through which both breathing gas for the patient supplied by the pressure generating device and exhalation gasses exhaled by the patient may flow. Gas flow region 180 includes a main orifice 182 that extends through faceplate portion 166. Main orifice 182 is defined by circular rim region 184 which, as described in greater detail below, is structured to be coupled to elbow conduit 164 so that main orifice can receive the flow of breathing gas therefrom. In addition, one or more holes 186 that extend through faceplate portion 166 are provided in the region that surrounds main orifice 182. In the exemplary embodiment, holes 186 are circular in shape, but other shapes are possible. The diameter of holes 186 may be, for example, from 0.5 mm to 2.5 mm. In one exemplary embodiment, sixty holes 186 are provided, wherein each hole has a diameter of 0.6 mm. In another exemplary embodiment, four holes 186 are provided, wherein each hole has a diameter of 2 mm.

Referring to FIG. 15, elbow conduit 164 includes an inlet end 188 having an inlet opening 190 structured to be connected to the hose connected to the pressure generating device. Elbow conduit 164 also includes an outlet end 192 having outlet opening 194 that is in fluid communication with inlet end 188 and inlet opening 190. Outlet end 192 is structured to be removeably and sealingly coupled to main orifice 184. In the example embodiment, outlet end 192 may be provided with an o-ring for providing an airtight seal. In addition, elbow conduit 164 includes a hood member 196 that surrounds outlet end 192. Hood member 196 is not in fluid communication with inlet opening 190, but rather engages the inner portion of outlet end 192 such that it defines an interior space 198 around outlet end 192 that is not in fluid communication with inlet opening 190. Hood member 196 includes a plurality of contacting edges 200 that define between them a plurality of openings 202, the purpose of which is described below.

Referring again to FIG. 12, elbow conduit 164 may be attached to 162 frame by inserting outlet end 192 into main orifice 182. When this is done, contacting edges 200 will contact the outer surface of faceplate portion 166, and in the exemplary embodiment will create a seal against that surface while leaving a gas flow path between the faceplate and the edge of elbow conduit at openings 202. In addition, as seen in FIG. 12, hood member 196 is disposed over holes 186 and main orifice 182.

In operation, breathing gas generated by the pressure generating device is delivered to patient interface device 160 through elbow conduit 164, and, in particular, inlet end 188 and outlet end 192 through main orifice 182. When the patient exhales, exhalation gasses pass through holes 182 and are captured and redirected by hood member 196 (which creates a chamber) and will be caused to pass to the atmosphere through openings 202, which diffuses the exhalation flow. Noise is created as the exhalation gasses pass through holes 186, and hood member 196 creates an insulating wall between the sound and the atmosphere to reduce noise and change the tone of the noise to a tone that is better tolerated by individuals located nearby. Also, hood member 196 causes the sound waves associated with the exhalation flow to be reflected, which results in some degree of noise cancellation.

FIG. 16 is a front isometric view of patient interface device 204 according to a further alternative embodiment. Patient interface device 204 is similar to patient interface device 160 and includes frame 206 having faceplate portion 208 and cushion 210 coupled thereto. Patient interface device 204 also includes an elbow conduit 212 that is similar in structure to elbow conduit 164 described elsewhere herein. As seen in As shown in FIG. 16, faceplate portion 208 includes a main orifice 214 that extends through faceplate portion 208. Main orifice 214 is defined by a circular rim region 216 that is structured to be coupled to an elbow conduit 212 so that main orifice 214 receives the flow of breathing gas therefrom. In addition, one or more tubular passageways 218 extend outwardly from and through faceplate portion 208 and are provided in the region that surrounds main orifice 214. When elbow conduit 214 is attached to faceplate portion 208, hood member 220 of elbow conduit 212 will overlie tubular passageways 218 and main orifice 214. In operation, breathing gas generated by the pressure generating device is delivered to patient interface device 204 through elbow conduit 212. Exhalation gasses pass through holes passageways 218 and are captured and redirected by hood member 220 (which creates a chamber) and will be caused to pass to the atmosphere through rectangular openings 222 of elbow conduit 212, which diffuses the exhalation flow.

FIG. 17 is an isometric view of a portion of a frame 224 according to another alternative embodiment that may be employed in the present invention. Frame 224 includes a faceplate portion 226 having a main orifice 228 that extends through the faceplate portion. Main orifice 228 is defined by a circular rim region 230 that is structured to be coupled to an elbow conduit as described herein so that main orifice 228 can receive the flow of breathing gas therefrom. In addition, one or more chamfered openings 232 extend outwardly from the interior of faceplate portion 226 and are provided in the region that surrounds main orifice 228.

Figure 18:
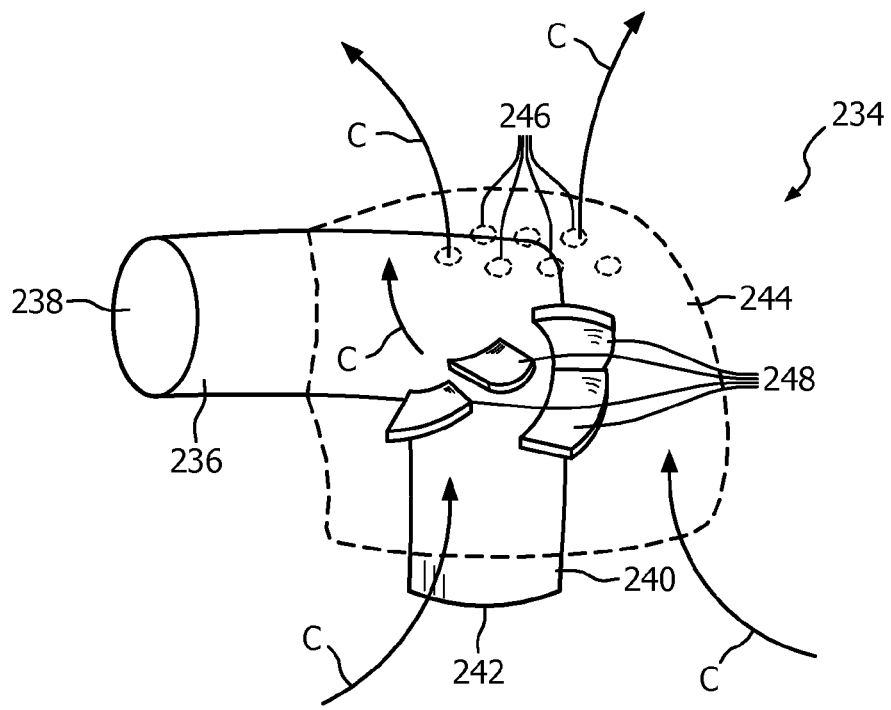
FIGS. 18 and 19 are side views of an alternative elbow conduit that may be employed in the present invention.

FIG. 18 is a right side view of an elbow conduit 234 according to another alternative exemplary embodiment of the present invention. Elbow conduit 234 may be employed with any of the frames describe herein. Elbow conduit 234 includes an inlet end 236 having an inlet opening 238 and an outlet end 240 having an outlet opening 242 that is in fluid communication with inlet end 236 and inlet opening 238. In addition, elbow conduit 234 includes a hood member 244 that surrounds outlet end 240. Hood member 244 is shown in phantom lines in FIG. 18 so that the other components of elbow conduit 234 can be readily seen.

Hood member 244 defines an interior space around outlet end 240 that is not in fluid communication with inlet opening 238. Hood member 244 also includes one or more holes 246 that extend through hood member 244. In the exemplary embodiment, hood member 244 includes a plurality of holes 246 that are spaced apart from an end portion 255 of hood member 244. Unlike the previous embodiments in which the exhaust gas was discharged to atmosphere at an area proximate to end portion 255, exhaust gas flowing into the hood member at end portion 255 flows to the other side of the hood member as indicated by arrows C. Also in the exemplary embodiment, holes 246 are oval-shaped, but other shapes are possible. Of course, other sizes, patterns, numbers, locations, internal geometries, and other noise reduction and/or flow dispersion characteristics for the holes are contemplated.

In a further embodiment, as shown in FIG. 18, elbow conduit 234 includes a series of baffle members 248 that are provided within the chamber created by hood member 244. Baffle members 248 deflect the exhalation flow and further quiet exhalation. In the illustrated embodiment, baffle members 248 are provided on outlet end 240. The present invention contemplates that they can be coupled to the elbow conduit at any location, such as being attached to the hood member. Baffle members 248 can also have any configuration, arrangement, pattern, size, shape, material, combination of materials, geometries, number of elements, orientation, or other characteristics that achieve the goal of minimizing noise and/or gas dispersion.

Figure 19:
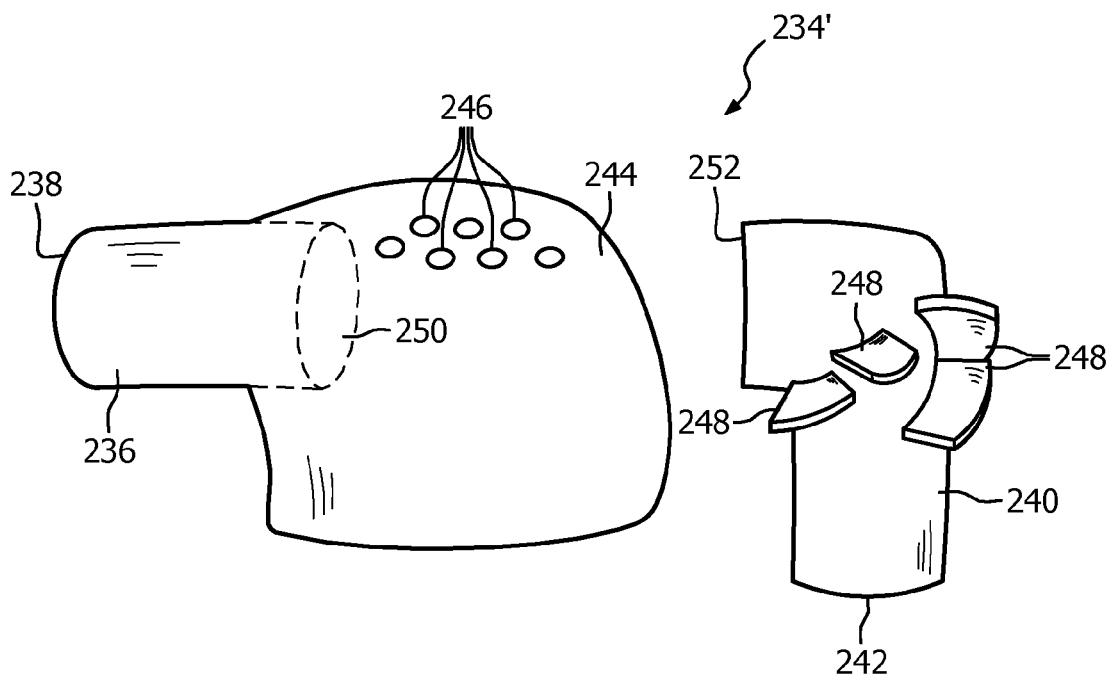

In the embodiment shown in FIG. 18, elbow conduit 234 is molded as a single piece or part. FIG. 19 shown an alternative embodiment of the elbow conduit, labeled with reference numeral 234', which is formed in two pieces that may fit together or otherwise coupled to form elbow conduit 234'. In particular, an end 250 may be friction fit into end 252 to form elbow conduit 234', which may then be attached to a frame as described elsewhere herein.

In the various embodiments described herein, hood members (44, 102, 196, 220, 244) may be made form a lower density material that has enhanced sound absorbing properties. Such materials may include, for example, Polycarbonate (PC), a Thermoplastic Elastomer (TPE), ABS, Polyamide (Nylon), Polypropylene (PP), Polyester (PET), foam, or another suitable sound absorbing material. In addition, baffle members 248 described above may be made of a material having enhanced sound reflecting properties.

As noted above, the size, shape, geometry, pattern, arrangement, configuration of the holes, both in faceplate, in the elbow conduit, or between the elbow conduit and the faceplate can be varied. For example, rather than multiple holes in the faceplate and/or the elbow conduit, one or more slits can be provided to define the gas flow path. Also, holes or other exhaust paths can be provided in all three locations, i.e., the faceplate, the elbow conduit, or between the faceplate and the elbow conduit.

Other materials or structures can be used with the holes/openings in faceplate, in the elbow conduit, or between the elbow conduit and the faceplate. For example, gas fabrics or meshes can be provided over all or a portion of one or more of these holes. The edges of one or more of these holes and the path defined by such holes can be varied. For example, these holes can be tapered so as to enhance diffusion of gas.

It can be appreciated that the present invention provides a patient interface device that provide the advantages of reduced exhalation noise, improved flushing of exhalation gasses, and/or diffuses gasses associated with exhalation flow (which reduces drafts).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A patient interface device, comprising:
   a cushion;
   a frame having a faceplate portion, the cushion being coupled to the frame, wherein the faceplate portion has a main orifice and a plurality of holes spaced around the main orifice, and wherein the main orifice and the plurality of holes extend through the frame; and
   a fluid coupling conduit having an inlet end, an outlet end fluidly coupled to the inlet end, and a hood member having one or more openings provided on an outer periphery thereof, wherein the inlet end is structured to receive a flow of breathing gas, wherein the outlet end is fluidly coupled to the main orifice to deliver the flow of breathing gas to the main orifice, and wherein the hood member surrounds the outlet end, is disposed over the plurality of holes, and engages the faceplate portion in a manner such that exhalation gasses will flow through the plurality of holes and be captured by the hood member and directed through the one or more openings.

2. The patient interface device according to claim 1, wherein the hood member includes a plurality of contacting edges that engage and seal against the faceplate portion, wherein the one or more openings comprises a plurality of openings, and wherein each of the openings is defined between a respective pair of the contacting edges.

3. The patient interface device according to claim 2, wherein each of the openings is a hemispherical opening or a rectangular opening.

4. The patient interface device according to claim 1, wherein the hood member includes an outer contacting edge that engages and seals against the faceplate portion, and wherein the one or more openings comprises a plurality of openings provided around an outer periphery of the hood member each at a location spaced from the outer contacting edge.

5. The patient interface device according to claim 4, wherein each of the holes is larger than each of the openings.

6. The patient interface device according to claim 4, wherein each of the holes is circular and has a first diameter and each of the openings is circular and has a second diameter, and wherein the first diameter is greater than the second diameter.

7. The patient interface device according to claim 1, wherein the main orifice comprises a main conduit extending outwardly from and through the faceplate portion.

8. The patient interface device according to claim 7, wherein the faceplate portion includes a recessed portion surrounding the main conduit, the plurality of holes being provided in the recessed portion, and wherein the outer contacting edge engages an outer edge of the recessed portion.

9. The patient interface device according to claim 1, wherein the main orifice comprises a main conduit extending through the faceplate portion, wherein the faceplate portion includes a recessed portion surrounding the main conduit, the plurality of holes being provided in the recessed portion, wherein a depth of the plurality of holes is equal to a thickness of the recessed portion.

10. The patient interface device according to claim 1, wherein the plurality of holes are each provided as part of a passageway member extending outwardly from and through the faceplate portion.

11. The patient interface device according to claim 1, wherein the plurality of holes are each provided as part of a chamfered member extending outwardly from and through the faceplate portion.

12. The patient interface device according to claim 1, wherein the fluid coupling conduit includes one or more baffle members provided in a chamber created by the hood member around the outlet end.

13. The patient interface device according to claim 1, wherein the fluid coupling conduit is a two-piece elbow conduit member having a first piece including the inlet end and the hood member and a second piece including the outlet end and the baffle members, and wherein the first piece and the second piece are structured to be selectively coupled to one another.

14. A method of controlling gas flow through a patient interface device, comprising:
 delivering a positive pressure flow of breathing gas to a patient through a coupling conduit fluidly coupled to a main orifice provided in a faceplate portion of the patient interface device;
 directing exhaled gasses exhaled by the patient to pass through a plurality of holes provided in the faceplate portion spaced around the main orifice;
 capturing the exhaled gasses in a chamber formed over the plurality of holes and the main conduit; and
 directing the exhaled gasses through one or more openings provided in the chamber to atmosphere.

15. The method according to claim 14, wherein the chamber is part of the coupling conduit.

16. The method according to claim 14, wherein the chamber is formed by a hood member forming a part of the coupling conduit, wherein a portion of the hood member engages and seals against the faceplate portion.

17. A patient interface device, comprising:
 a cushion;
 a frame having a faceplate portion, the cushion being coupled to the frame, the faceplate portion having a main orifice and a plurality of holes spaced around the main orifice, the main conduit and the plurality of holes extending through the frame and being in fluid communication with the cushion; and
 a fluid coupling conduit having an inlet end, an outlet end terminating in an outlet opening, the outlet end being fluidly coupled to the inlet end, and a deflector member provided around an at least a portion of an outer periphery of the outlet end at a location spaced from the outlet opening, wherein the inlet end is structured to receive a flow of breathing gas, wherein the outlet end is fluidly coupled to the main orifice to deliver the flow of breathing gas to the main orifice through the outlet opening, and wherein the deflector member is positioned over the plurality of holes in a manner wherein exhalation gasses will flow from the cushion, through the plurality of holes and will be redirected and diffused by the deflector member and be caused to flow around the outlet end to atmosphere.

18. The patient interface device according to claim 17, wherein the deflector member is arc shaped.

19. The patient interface device according to claim 17, wherein the main orifice comprises a main conduit extending outwardly from and through the faceplate portion.

20. The patient interface device according to claim 17, wherein the plurality of holes are each provided as part of a passageway member extending outwardly from and through the faceplate portion.

* * * * *